(12) United States Patent
Ju et al.

(10) Patent No.: US 7,990,161 B2
(45) Date of Patent: Aug. 2, 2011

(54) APPARATUS FOR MEASURING TOTAL ACID NUMBER OF OIL AND ESTIMATING LIFETIME OF OIL, AND METHOD FOR MEASURING TOTAL ACID NUMBER OF OIL AND OIL SENSOR USING THE SAME

(75) Inventors: Byeong Kwon Ju, Seoul (KR); Kyung Shin, Seoul (KR); Cheol Ho Yeo, Uijeongbu (KR)

(73) Assignees: SNS Revolution Co., Ltd., Seoul (KR); Korea University Industrial & Academic Collaboration Foundation, Seoul (KR)

( * ) Notice: Subject to any disclaimer, the term of this patent is extended or adjusted under 35 U.S.C. 154(b) by 196 days.

(21) Appl. No.: 12/514,655

(22) PCT Filed: Oct. 31, 2007

(86) PCT No.: PCT/KR2007/005419
§ 371 (c)(1),
(2), (4) Date: May 13, 2009

(87) PCT Pub. No.: WO2008/060052
PCT Pub. Date: May 22, 2008

(65) Prior Publication Data
US 2010/0052702 A1     Mar. 4, 2010

(30) Foreign Application Priority Data

Nov. 16, 2006  (KR) .................. 10-2006-0113233
Oct. 24, 2007  (KR) .................. 10-2007-0107098

(51) Int. Cl.
*G01R 27/08* (2006.01)
*G01N 27/416* (2006.01)
(52) U.S. Cl. ........................... 324/698; 324/459
(58) Field of Classification Search .................. 324/698, 324/459
See application file for complete search history.

(56) References Cited

U.S. PATENT DOCUMENTS

2007/0208243 A1   9/2007  Gabriel et al.
2008/0143351 A1*  6/2008  Lee et al. ..................... 324/698

FOREIGN PATENT DOCUMENTS

| JP | 6-201649 A | 7/1994 |
| KR | 10-2006-0108427 A | 10/2006 |
| KR | 10-0648423 B1 | 11/2006 |

* cited by examiner

*Primary Examiner* — Vincent Q Nguyen
(74) *Attorney, Agent, or Firm* — Drinker Biddle & Reath LLP

(57) ABSTRACT

Disclosed herein are an apparatus for measuring the total acid number of oil, an apparatus for measuring the lifetime of oil through the measurement of the total acid number of oil, a method for measuring the total acid number of oil, and a method of making measurements using an oil sensor. According to the disclosed invention, measurement accuracy can be increased through the use of a high-sensitivity conductance measuring sensor, the inventive apparatus can be applied to both lubricant oil and insulating oil, the size of the total acid number-measuring apparatus can be reduced.

39 Claims, 8 Drawing Sheets

APPARATUS FOR MEASURING TOTAL ACID NUMBER OF OIL AND ESTIMATING LIFETIME OF OIL, AND METHOD FOR MEASURING TOTAL ACID NUMBER OF OIL AND OIL SENSOR USING THE SAME

CROSS-REFERENCE TO RELATED APPLICATIONS

This application is the U.S. national phase of the International Patent Application No. PCT/KR2007/005419 filed Oct. 31, 2007, which claims the benefit of Korean Application No. 10-2006-0113233 filed Nov. 16, 2006 and Korean Application No. 10-2007-0107098, filed Oct 24, 2007, the entire content of each is incorporated herein by reference.

TECHNICAL FIELD

The present invention relates to an apparatus for measuring the total acid number of oil, and more particularly to an apparatus for measuring the total acid number of oil, an apparatus for estimating the lifetime of oil through the measurement of the total acid number of oil, and a method for measuring the total acid number of oil.

Generally, oil shows a phenomenon in which the properties and functions thereof deteriorate with the passage of time. This phenomenon is called a "deterioration phenomenon", and the most important cause of deterioration is oxidation. In the case of lubricant oil, deterioration in lubricant function, such as increases in mechanical corrosion and friction, occur, and in the case of insulating oil, remarkable deterioration in insulating function, such as electrical insulation breakdown and a reduction in the dispersion of generated heat, occurs. A reference value indicating the degree of such oxidation is called "total acid number". Thus, the total acid number is a basis for grasping the functional state. The oxidation of oil increases suddenly after it occurs slowly for a given period of time, and accelerates particularly due to light and heat.

The main components are mostly hydrocarbons extracted from mineral oil. Thus, oil undergoes a chemical reaction, initiated by heat and light, and generally, the same oxidation reaction occurs.

BACKGROUND ART

In Stefan Korcek et al., Ind. Eng. Chem. Prod. Res. Dev., Vol. 25, No. 4, 1986, the oxidation mechanism of internal combustion engine oil is described in detail, and the literature describes the continuous production of peroxides by oxygen in the oxidation reaction. Also, S. S. Wang, Sensors and Actuators B, 17, pp. 179-185, 1994, describes the correlation between engine oil and TAN, and the lifetime of engine oil.

Regarding carbon nanotubes, Philip G., SCIENCE, VOL 287 10, 2000, reports that carbon nanotubes can be used as oxygen gas sensor materials, and J. Wang, Journal of the American Chemical Society. 125. pp. 2408, 2003, reports that carbon nanotube electrodes were used to measure hydrogen peroxide. This is because carbon nanotubes have good reactivity with oxygen. Carbon nanotubes have an $sp_2$-bonded tubular structure of graphite, leading to a very large surface area per unit area, and thus show excellent ability to adsorb gaseous molecules or ions. Also, carbon nanotubes show the electrical properties of metals or semiconductors and have a property in which the conductance thereof changes with the adsorption of gaseous molecules or ions thereon.

Moreover, carbon nanotubes have advantages in that they have a small size and, at the same time, the ability to adsorb and store ions, show high sensitivity and response speed due to the large surface area per unit area thereof, and are excellent in physical chemical durability.

FIGS. 1a and 1b show the structure of a prior conductance-measuring sensor unit comprising carbon nanotubes. As shown in the figures, the measuring sensor unit comprises an electrode 32, to which power is applied, a conductance sensing film 31, which is applied on the electrode 32, and a substrate 33 so as to sense the electrochemical change of oil, and is formed of carbon nanotubes, and the substrate 33 on which the conductance sensing film 31 and the electrode 32 are placed. In the structure of the underlying electrode 32, there is difficulty in alignment due to opacity in an opaque silk screen process, and thus there are problems related to thickness control and smoothness.

A method for fabricating the conductance sensing unit having the above structure is as follows.

First, a step of mixing, heating and melting a binder and alpha-terpineol, that is, a step of mixing ethyl cellulose and alpha-terpineol at a given ratio, and heating and melting the mixture, is carried out.

A step of mixing carbon nanotubes with a heated and melted mixture of glass frit and alpha-terpineol, such that the carbon nanotubes can be maintained at a given viscosity, is carried out.

Then, a step of patterning the underlying electrode on the substrate using a vacuum deposition method, such as an E-beam evaporator or a sputtering method, or a screen printing method, is carried out.

Finally, a step of screen-printing the carbon nanotubes on the substrate having the underlying electrode patterned thereon, and sintering the printed carbon nanotubes, is carried out.

FIG. 2 shows the deterioration characteristics of oil, measured with a sensor fabricated according to the prior art, and FIGS. 3a and 3b are graphic diagrams showing the change in values caused by the influence of temperature in a prior oil sensor measurement method and the change in pattern of sensor output values caused by oil replacement, respectively.

As shown in FIG. 2, it can be seen that, in the values measured using the prior underlying electrode structure, the pattern of resistance measurement values definitely changes with running distance.

In the case of the conductance measuring sensor unit fabricated using carbon nanotubes through the above-described steps, when the deterioration of oil is measured, the initial sensor values differ between the sensors, and thus the ratio of the final measurement value to the initial measurement value is different for each of the sensors. Thus, in this case, in order for data values determining the degree of deterioration to be precisely measured according to the kind of oil and manufactured sensor, a very wide range of measurement data is required.

Generally, a sensor comprising a CNT sensor film is fabricated to have an initial value of about 0.5-20 kΩ. Conductance or electrical resistance, actually measured in oil, changes according to the condition of oil. Sensors having a low initial value have a small change in measurement values, and sensors having a relatively large change in measurement values have a somewhat large change in measurement values.

In the prior art, a conventional sensing method adopts a method of analyzing a change in oil condition (using absolute values) and comparing the analyzed values to reference data. If initial values are different between sensor products, the reference database will require a very vast amount of data according to a fabricated sensor, and thus a large amount of time and effort will be required to make the database.

In the prior art, due to the above-described problems, a method of sensing the condition of oil using an oil sensor comprising a CNT sensor film is used, and a method of sensing the change in condition of oil by recognizing the slope pattern of measurement values of a sensor is also used. However, in this case, the oil sensor having the CNT sensor film is greatly influenced by temperature, and thus recognizing the slope pattern involves significant errors. Also, once the oil sensor having the CNT sense film is used, it cannot be returned to the initial value state of oil, when oil is replaced with fresh oil. Thus, the data that is first measured and the data that is subsequently measured are different from each other, and in this case, the slope patterns of the measurement values are different, leading to significant errors.

Meanwhile, a prior method for measuring total acid number has problems in that a measurement apparatus is difficult to fabricate due to its complex structure and large size, and is sensitive to noises, leading to erroneous output.

In addition, in the prior art, there is a problem in that real-time measurement is difficult, because the measurement of total acid number and other properties of oil is performed using a measurement sensor in an operation-stopped state or a state in which the operation of a transformer is stopped.

DISCLOSURE

Technical Problem

A first object of the present invention, which is to provide an apparatus for measuring the total acid number of oil, which has increased accuracy through the use of a high-sensitivity conductance measuring sensor, can be applied to both lubricant oil and insulating oil, and has a reduced size and a simple structure.

A second object of the present invention is to provide an apparatus for estimating the lifetime of oil through the measurement of the total acid number of oil, which can precisely estimate the lifetime of oil using the apparatus for measuring the total acid number of oil, and allows systems that use oil to be managed and maintained in optimal conditions.

A third object of the present invention is to construct said total acid number-measuring apparatus such that it can measure the conductance of oil in a real-time state, in which vehicles are running, or in which devices are in operation, rather than in an operation-stopped state.

A fourth object of the present invention is to construct a conductance-measuring sensor unit such that alignment and thickness control are easy, in which the conductance-measuring sensor unit has a structure obtained by forming a sensing film on a substrate and then depositing an overlying electrode thereon.

A fifth object of the present invention is to provide a method of conducting measurement using an oil sensor comprising a CNT sensor film, in which precise measurement having relatively low errors can be achieved by measuring the condition of oil as a ratio to an initial value (Sout/Sint).

Technical Solution

To achieve the above objects, the present invention provides an apparatus for measuring the total acid number of oil, the apparatus including: a unit for storing a total acid number table, in which a change in conductance and the corresponding measurement values of total acid number and physical properties of oils are matched; a unit for measuring the conductance of said oils, including lubricant oil and insulating oil; a total acid number-determining unit for searching the total acid number table to determine total acid number and physical properties according to the measured conductance and outputting the determined total acid number or physical property values of oils, or information about the determined total acid number or physical properties; wherein the unit for measuring conductance includes: a substrate formed to have a given area; a plate-shaped conductance sensing film for measuring the conductance of oils, in which the sensing film is formed by screen-printing carbon nanotubes on the upper surface of the substrate and sintering the printed carbon nanotubes; an overlying electrode patterned using a vacuum deposition method such that it extends on the upper surface of the sensing film or extends from the upper surface of the sensing film to the upper surface of the substrate and is connected to an external power source.

The inventive apparatus preferably additionally includes a temperature sensor, which serves to measure the temperature of oils and has a temperature range set such that the oil sensor is operated at 40° C. to 120° C.

Also, a plurality of holes is preferably formed in the plate-shaped sensing film, formed by screen-printing carbon nanotubes on the upper surface of the substrate and sintering the printed carbon nanotubes.

Moreover, the substrate is preferably any one selected from among a glass substrate, a silicon substrate and a sintered alumina substrate, and the power source is preferably a direct current power source.

Also, the physical properties are viscosity and total base value for lubricant oil, and insulating strength, water content and volume resistivity for insulating oil.

Furthermore, when the carbon nanotubes are screen-printed, the conductance sensing film has a thickness of 1-990 μm.

In another aspect, the present invention provides an apparatus for measuring the lifetime of oils through the real-time measurement of the total acid number of oils, the apparatus including: a unit for storing a total acid number table in which a change in conductance, the use period of oils and the corresponding measurement values of total acid number and physical properties of oils are matched; a sensing unit for measuring the conductance of oils, including lubricant oil and insulating oil; a total acid number-determining unit for searching the total acid number table to determine total acid number and physical properties according to the determined conductance and outputting the measured total acid number or physical properties of oils, or information about the determined total acid number or physical properties; an expected lifetime-estimating unit for searching the table to determine the use period of oils corresponding to the total acid number information and producing the estimated lifetime information of oils using the determined use period, wherein the unit for measuring conductance includes: a substrate, formed to have a given area; a plate-shaped conductance sensing film for measuring the conductance of oils, in which the sensing film is formed by screen-printing carbon nanotubes on the upper surface of the substrate and sintering the printed carbon nanotubes; an overlying electrode patterned using a vacuum deposition method such that it extends on the upper surface of the sensing film or extends from the upper surface of the sensing film to the upper surface of the substrate, and is connected to an external power source.

In the inventive apparatus for estimating the lifetime of oils, a plurality of holes is preferably formed in the conductance sensing film.

In addition, the inventive apparatus preferably additionally includes a visual information display unit for visually displaying the estimated lifetime information using at least one of letters or images.

Moreover, the inventive apparatus preferably additionally includes: a threshold determining unit for producing replacement request information when the estimated lifetime information is shorter than the pre-stored lifetime threshold of oils; and a warning sound output unit for outputting an oil replacement warning sound message.

In still another aspect, the present invention provides a method for measuring the total acid number of oils, the method including: making a unit for storing a total acid number table, in which a change in conductance and the corresponding total acid number and physical properties of oils are matched; measuring the conductance of oils using a plate-shaped conductance sensing film, obtained by screen-printing carbon nanotubes on the upper surface of a substrate and sintering the printed carbon nanotubes, and an overlying electrode, patterned using a vacuum deposition method such that it extends over the upper surface of the sensing film or extends from the upper surface of the sensing film to the upper surface of the substrate and is connected to an external power source; and searching the table to determine the total acid number or physical properties according to the measured conductance and outputting the determined total acid number or physical properties or information about the determined total acid number or physical properties.

In the inventive method, the conductance sensing film preferably has a plurality of holes formed therein.

Also, the vacuum deposition method is preferably an E-beam evaporator or a sputtering method.

In still another aspect, the present invention provides a method of making measurements with an oil sensor including a CNT (carbon nanotube) sensing film, the method including: storing an initial sensor value (Sint) in air in order to measure the state of oil; constructing, in a total acid value table, a database in which a total acid value is matched according to the sensing value (Sout/Sint) of the sensor; converting a measured value (Sout) of a change in the state of oil to the sensing value (Sout/Sint); and comparing the sensing value to information in the database.

ADVANTAGEOUS EFFECTS

As described above, the present invention provides an apparatus for measuring the total acid number of oil, which has increased accuracy through the use of a high-sensitivity conductance measuring sensor, can be applied to both lubricant oil and insulating oil, and has a reduced size and a simple structure. Also, the present invention provides an apparatus for estimating the lifetime of oil through the measurement of the total acid number of oil, which can precisely estimate the lifetime of oil using the apparatus for measuring the total acid number of oil, and allows systems that use oil to be managed and maintained under optimal conditions.

Moreover, the present invention provides a method of making measurements using an oil sensor including a CNT sensor film, in which precise measurements having relatively small errors can be made by measuring the condition of oil as a ratio to an initial value (Sout/Sint).

In addition, according to the present invention, a conductance-measuring sensor unit can be constructed such that alignment and thickness control are easy, in which the conductance-measuring sensor unit structure is obtained by forming a sensing film on a substrate and then depositing an overlying electrode thereon.

DESCRIPTION OF IMPORTANT REFERENCE NUMERALS IN THE FIGURES

110: conductance-measuring sensor unit;
120: unit for storing total acid number table;
130: unit for determining total acid number;
210: conductance-measuring sensor unit;
215: temperature sensor;
220: unit for storing total acid number table;
230: unit for determining total acid number;
240: unit for estimating expected lifetime;
250: visual information display unit;

260: threshold determining unit;
270: warning sound output unit;
310: conductance sensing film;
320: electrode; 330: substrate;
350: holes; and 360: circular holes.

Mode For Invention

The present invention provides a method of fabricating a high-sensitivity sensor device using carbon nanotubes, and an apparatus and method for measuring the change in the total acid number of oil by detecting the function of oil as an electrical conductance signal using the fabricated device, and determining the total acid number of oil according to correlation with a pre-measured total acid number (TAN).

The present invention relates to an apparatus and method for measuring the change in the total acid number of oil and the physical properties of oil using carbon nanotubes, in which the degree of oxidation of lubricant oil and insulating oil is outputted through the change in conductance of carbon nanotubes, and is measured by comparing the outputted change with the initially measured conductance and converting the change in conductance to total acid number. The present invention provides an algorithm for measuring the total acid number of oil, a carbon nanotube sensor for measuring the conductance of oil and a fabrication process thereof, and a control and output circuit for outputting compared conductance.

Hereinafter, preferred embodiments of the present invention will be described with reference to the accompanying drawings.

Figure 4A:
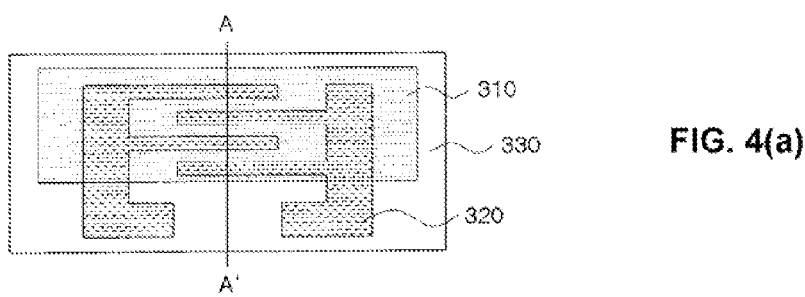
FIGS. 4a and 4b are a plane view and a cross-sectional view, which show an example of a conductance-measuring sensor unit according to the present invention.
Figure 4B:
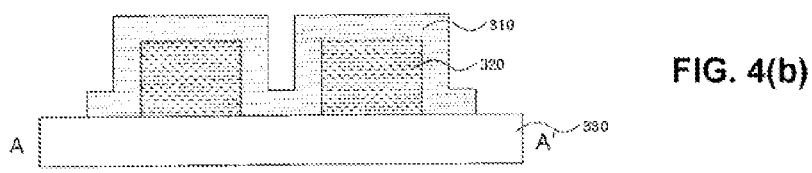

FIGS. 4a and 4b show a first embodiment of a conductance-measuring sensor unit. As shown in the figures, the conductance-measuring sensor unit includes an electrode 320 to which power is applied, a conductance sensing film 310, which is continuously applied over the electrode 320 and a substrate 330, and is formed of carbon nanotubes for sensing the electrochemical change of oil, and the substrate 330, on which the conductance sensing film 310 and the electrode 320 are placed.

The conductance sensing film 310 is provided to measure the conductance of oil, and has a continuous plate-shaped structure having no empty space in order to increase the contact area between the sensing film and oil. That is, the conductance sensing film 310 is formed without any empty space, over the electrodes 320, between the electrodes 320, or over the substrate 330. This leads to an increase in sensitivity.

The principle and method of measurement using the conductance measuring sensor unit shown in FIGS. 4a and 4b are as follows. Carbon nanotubes show a very sensitive response to oxidative or reducing materials and show the phenomenon that the conductance thereof increases in the presence of oxidative materials. Thus, because oxidation plays a very important role in the deterioration phenomenon of oil, and an increase in the deterioration of oil leads to an increase in the amount of oxygen on the carbon nanotube sensor film, resulting in an increase in conductance. Herein, because the carbon nanotubes have a given conductance value depending on the amount of oxygen in oil, the conductance value is previously measured, and the measured value is set as reference data and is used as information for determining total acid number on the basis of a change obtained by comparing the measured conductance with conductance output from the sensor.

The method for fabricating the above carbon nanotube sensor comprises the steps of: depositing the electrode 320 on the substrate 330 using a shadow mask or fabricating the electrode 320 by printing a metal paste on the substrate; screen-printing a carbon nanotube paste on the resulting substrate to fabricate the conductance sensing film 310; and sintering the fabricated device. Preferably, the conductance of oil may be controlled by a temperature sensor so that conductance can be measured within a given temperature range. Herein, the substrate of the device is a glass substrate, a silicon substrate or a sintered alumina substrate.

The electrode 320 can be fabricated using a deposition system, such as an E-beam or a sputter, through a shadow mask, or by screen printing Ag or other metal pastes. The conductance sensing film 310 is formed by screen-printing a paste consisting of a mixture of carbon nanotube powder and a binder. The carbon nanotube film, formed on the substrate 330 using the screen printing method, serves as the conductance sensing film 310, which is connected between the electrodes 320. The device thus fabricated is connected to a DC power source, such that electric current flows through the conductance sensing film 310, and the conductance sensing film 310 is brought into oil.

This conductance sensing film 310 outputs the change in conductance, converted from the electrochemical change of oil. A process of preparing the carbon nanotube paste using the screen printing technique comprises the steps of: (1) mixing a binder and alpha-terpineol and heating and melting the mixture; (2) mixing carbon nanotubes with a heated and melted mixture of glass frit and alpha-terpineol; and (3) patterning the electrode on the substrate, and then screen-printing the carbon nanotubes on the substrate and sintering the printed carbon nanotubes.

Figure 5A:
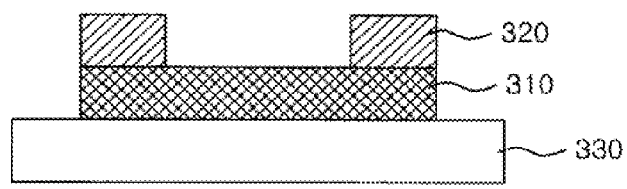
FIGS. 5a and 5b are cross-sectional views showing the structure of a first embodiment of the conductance-measuring sensor unit according to the present invention.
Figure 5B:
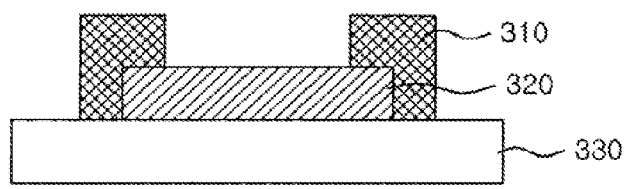

FIGS. 5a and 5b shows a second embodiment of the present invention, in which the conductance sensing film 310 is first formed on the upper surface of the substrate and the overlying electrode 320 is then formed on the conductance sensing film and the substrate 330.

The sensor unit having this structure is fabricated in a manner different from that of the prior art, and the fabrication method thereof is as follows.

First, a step of mixing a binder and alpha-terpineol and heating and melting the mixture is carried out. That is, a step of mixing ethyl cellulose and alpha-terpineol at a given ratio and heating and melting the mixture is carried out.

Then, a step of mixing carbon nanotubes with a heated and melted mixture of glass frit and alpha-terpineol, such that the carbon nanotubes can maintain a given viscosity, is carried out.

Then, a step of screen-printing the carbon nanotubes on the substrate 330 and sintering the printed carbon nanotubes is carried out.

Finally, a step of patterning the electrode 320 on the substrate 330 using a vacuum deposition method using an E-beam evaporator or sputtering method is carried out.

The screen printing technology is a technology of printing carbon nanotubes using a patterned film, which is a silk screen. In the prior art, when the prepared carbon nanotube paste was printed, the patterned portion of the silk screen was discolored black, because the carbon nanotube powder had a black color. Thus, if the carbon nanotube paste is screen-printed on the underlying electrode, the first screening printing step can be easily carried out, but there is a problem in that it is difficult to align a subsequently screen-printed layer with the underlying electrode. However, as in the process of the second embodiment, when the step of depositing the overlying electrode 320 is carried out after the carbon nanotube paste is screen-printed on the substrate 330, there are advantages in that it is possible to align all devices and the size of the sensing film 310 can be easily controlled. Particularly, in the sensors fabricated using these two technologies, the overlying electrode 320 can achieve a yield (an error of 5%) of more than 80% in the case where 150 devices are formed on a 4-inch wafer, whereas the yield of the underlying electrode is only about 15. Thus, according to the present invention, reliable sensors can be fabricated in large amounts.

Figure 1A:
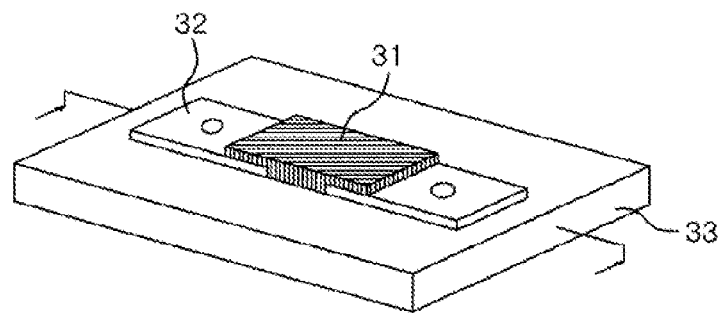
FIGS. 1a and 1b show a perspective view and cross-sectional view of a sensor unit fabricated according to the prior art.
Figure 1B:
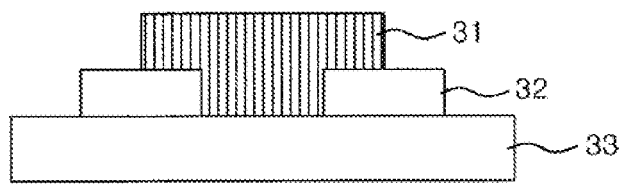
Figure 2:
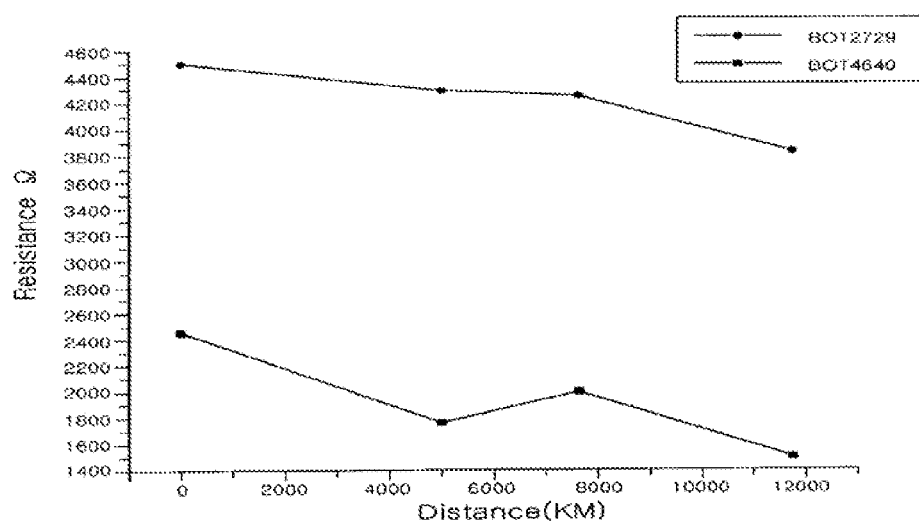
FIG. 2 shows the deterioration characteristics of oil, measured with a sensor fabricated according to the prior art.
Figure 3A:
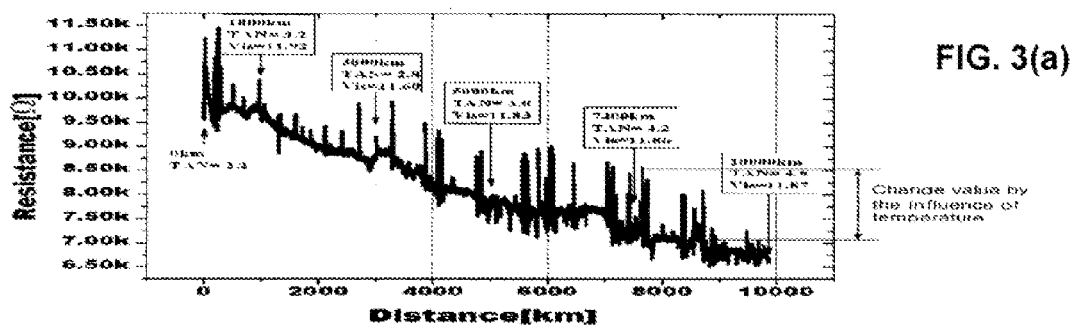
FIGS. 3a and 3b show the change in measurement value, caused by the influence of temperature, in the prior oil sensor measurement method, and the change in sensor output value, caused by oil replacement.
Figure 3B:
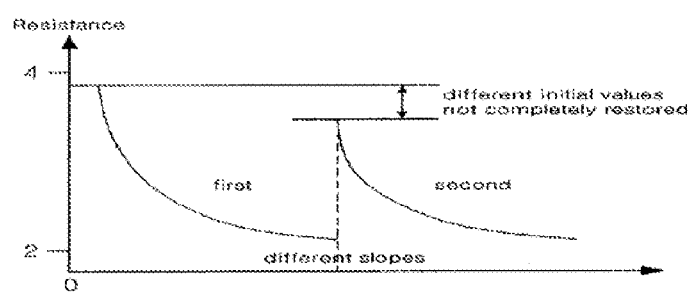
Figure 6:
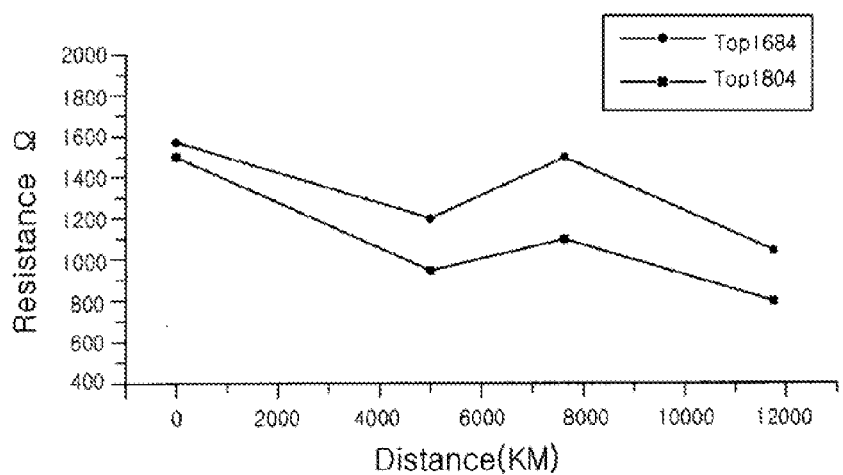
FIG. 6 shows the deterioration characteristics of oil, measured with a sensor fabricated according to the first embodiment of the inventive conductance-measuring sensor unit.

Particularly, the measured deterioration characteristics of the sensor unit, fabricated according to the second embodiment of the present invention, are shown in FIG. 6. It can be seen that the graphs of FIG. 6 show uniform characteristics compared to those of FIG. 2, measured using the sensor unit fabricated according to the prior art. Thus, it can be seen that the sensor fabricated according to the second embodiment of the present invention has highly stable and reliable characteristics.

When the deterioration of oil is measured with the sensor unit fabricated according to the prior art, the ratio of the finally measured value to the initial value differs between the sensors, because the initial measurement values of the sensors are different. Thus, in this case, in order for data values for determining the degree of deterioration to be precisely measured according to the kinds of oils and fabricated sensors, a very large amount of measurement data is required.

However, when the degree of deterioration of oil is measured with the sensor unit fabricated according to the second embodiment of the present invention, the ratio of the final measurement value to the initial measurement value of the sensor is constant, because the inventive sensor is fabricated with little or no error, and the initial value of the sensor is constant. Accordingly, more precise measurement than in the prior art is possible, and sensing errors can be minimized, thus increasing measurement reliability.

Figure 7A:
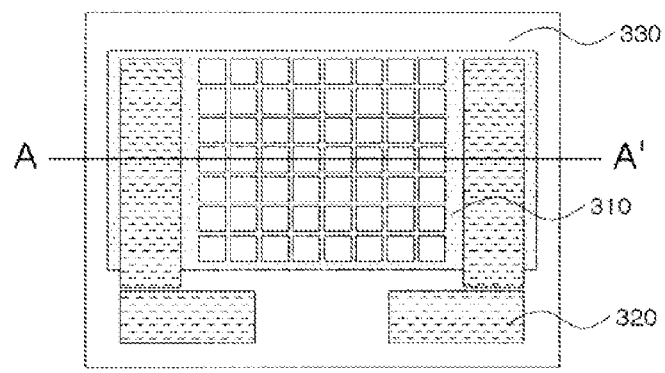
FIGS. 7a and 7b are a plane view and a cross-sectional view, which show the structure of a first embodiment of the conductance-measuring sensor unit according to the present invention.
Figure 7B:
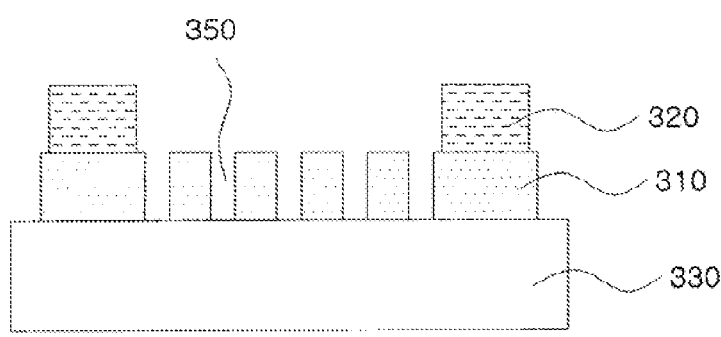

A third embodiment of the present invention indicates another example of the conductance measuring sensor unit according to the present invention, and is shown in FIGS. 7a and 7b. As shown in the figures, the sensor unit of the third embodiment is fabricated in the same manner as in the process of the second embodiment, except that a plurality of holes 350 is formed in the sensing film 310 in the step of patterning the screen-printed material.

Herein, the shape of the holes 350 is not limited to any specific shape, such as a square, circular or lozenge shape, and the holes 350 can be formed into various shapes depending on the sizes of the sensor, the substrate and the sensing film.

In the case of the sensor unit fabricated according to the third embodiment of the present invention, the sensing efficiency can be increased by greatly increasing the surface area of the sensing film 310 compared to the prior art.

The sensing film 310 fabricated in the third embodiment is fabricated to a thickness ranging from a few tens of μm to a few hundreds of μm using the screen printing method, and the holes 350 in the sensing film 310 can be formed in the shape of squares having a width of 50 μm to a few hundreds of μm, thus increasing the surface area of the sensing film.

Figure 8:
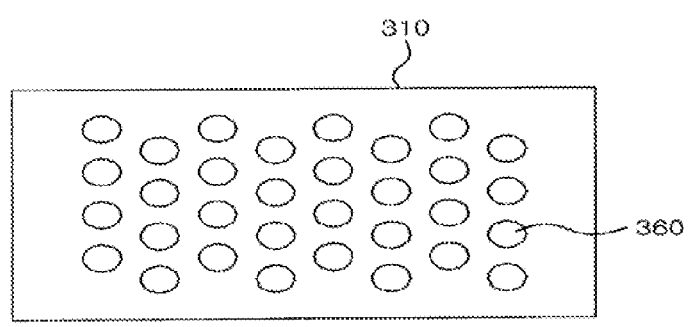
FIG. 8 is a plane view showing the structure of a third embodiment of the conductance-measuring sensor unit according to the present invention.

FIG. 8 shows another embodiment in which the holes 350 in the sensing film 310, fabricated in the third embodiment, are formed in a circular shape. The plurality of such circles 360 can be arranged such that they cross each other, and thus the internal area of the sensing film can be increased, leading to an increase in the internal density of the sensing film 310, thus further increasing the sensing efficiency of the sensing film.

Hereinafter, an apparatus for measuring the total acid number lifetime of oil using the inventive conductive-measuring sensor unit having the above-described construction and characteristics, a method for measuring the total acid number of oil using the sensor unit, and a method of conducting measurement with an oil sensor, will be described in detail.

Figure 9:
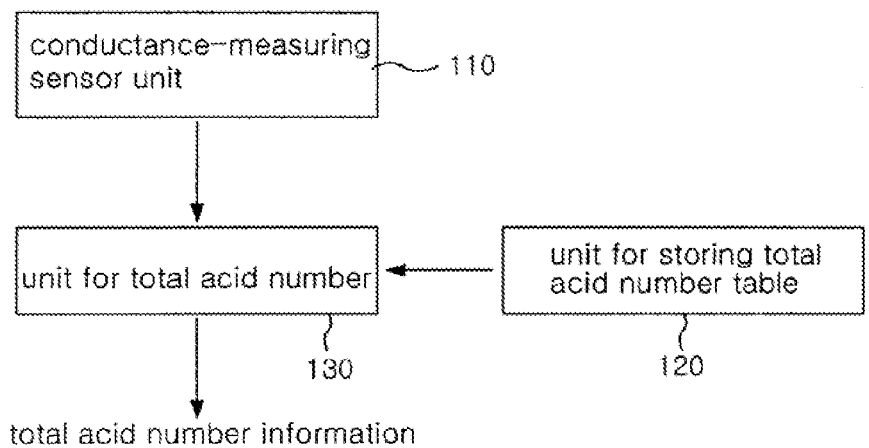
FIG. 9 is a block diagram of an apparatus for measuring the total acid number of oil according to one embodiment of the present invention.

FIG. 9 is a block diagram of an apparatus for measuring the total acid number of oil according to one embodiment of the present invention.

As shown in FIG. 9, a conductance measuring sensor unit 110 measures the conductance of oil. Herein, the conductance measuring sensor unit 110 comprises: a substrate formed to have a given area; a plate-shaped conductance sensing film, which serves to measure the conductance of oil and is formed by screen-printing carbon nanotubes on the upper surface of the substrate and sintering the printed carbon nanotubes; and an overlying electrode, which extends over the upper surface of the sensing film or extends from the upper surface to the upper surface of the substrate and is patterned using a vacuum deposition method so as to be connected to an external power source. Herein, oils that are used in this embodiment may include lubricant oil and insulating oil.

A unit 120 for storing a total acid number table stores a total acid number table in which a change in conductance and the corresponding total acid number are matched. The unit 120 for storing the total acid number table includes any one among volatile memory devices or nonvolatile memory devices, and stores the total acid number table in a database format.

A total acid number output unit 130 searches the total acid number table to determine the total acid number according to the measured conductance, and outputs the total acid number information of oil. The total acid number output unit 130 comprises a means for searching the memory of the total acid number storage unit 120 and a means for comparing the searched information with the measured conductance value to estimate the total acid number of oil. Such means can be embodied with an interface for memory access, at least one microprocessor, and a firmware having a driving program therein.

Figure 10A:
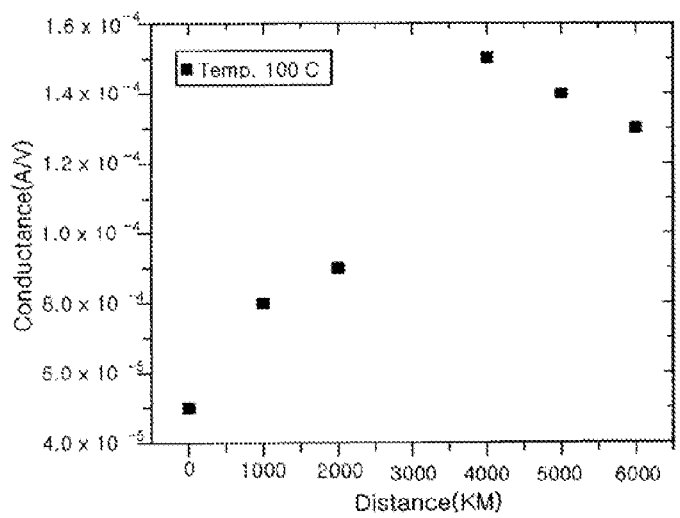
FIGS. 10a and 10b are graphic diagrams showing the changes in conductance and total acid number according to running distance, in one example of a process of producing a total acid number table
Figure 10B:
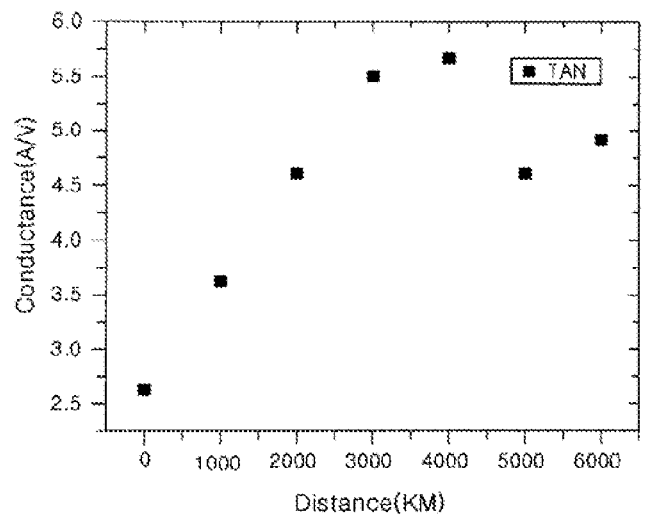

FIGS. 10a and 10b are graphic diagrams showing the changes in conductance and total acid number as a function of running distance, in an example of a process of determining total acid number.

In FIG. 10a, the x-axis is running distance, and the y-axis is conductance value. In FIG. 10b, the x-axis is running distance, and the y-axis is total acid number.

For example, it can be estimated that, when the conductance of oil, having a conductance of 5.0×E-5 upon oil injection, and a total acid number of 2.6 changes to 8.0×E-5, the total acid number will be about 3.55. This matching correlation between conductance and total acid number can be stored as the total acid number table. The process of producing the total acid number table requires repeated experiments under various experimental conditions. Also, the total acid number table is databased as a result of such repeated experiments, and once it is stored, it is preferably not changed during the operation of the total acid number-measuring apparatus.

Table 1 below shows an example of the total acid number table of each of lubricant oil and insulating oil.

TABLE 1

| Total acid number (TAN) | Conductance | |
| --- | --- | --- |
| | Lubricant oil | Insulating oil |
| 0.09 | — | 5.70E−04 |
| 0.11 | — | 2.01E−04 |
| 1.32 | 3.51E−05 | |
| 1.51 | 4.18E−05 | |
| 1.54 | 4.29E−05 | |

TABLE 1-continued

| Total acid number (TAN) | Conductance | |
| --- | --- | --- |
| | Lubricant oil | Insulating oil |
| 1.66 | 4.66E−05 | |
| 1.89 | 5.71E−05 | |
| 2.07 | 8.29E−05 | |
| 2.24 | 6.85E−05 | |
| 2.29 | 7.92E−05 | |
| 2.38 | 7.82E−05 | |
| 2.40 | 7.17E−05 | |
| 3.54 | 9.23E−05 | |

As can be seen in Table 1, there are cases in which the changes in conductance and total acid number are not linear. Preferably, in the process of searching the total acid number table, current total acid number can be estimated by recording the change in previous conductance and referring to all of the change in current conductance and the change in previous conductance.

Also, with respect to the deterioration in function of oil, the major parameters of physical properties can vary depending on the kind of oil. Factors that are used to examine the deterioration phenomenon, indicating that the lubricant function of oil is reduced, include viscosity, total acid number, total base number and the like. Among them, the factor that is most closely connected with the lubricant function may be viscosity. The correlation between conductance, total acid number and viscosity, which are used to examine the state of lubricant oil, is shown in Table 2 below.

TABLE 2

| Conductance | Total acid number (TAN) | Viscosity [100° C., cst] |
| --- | --- | --- |
| 1.163E−04 | 2.8 | 11.7 |
| 1.290E−04 | 3 | 11.78 |
| 1.353E−04 | 3.2 | 11.83 |
| 1.408E−04 | 4.2 | 11.86 |
| 1.493E−04 | 4.8 | 11.87 |

Meanwhile, factors that are used to examine the insulating function of insulating oil include insulating strength, water content, volume resistivity and the like. Among them, the most typical factor used to examine the insulating function is insulating strength. The correlation between total acid number, insulating strength and conductance is shown in Table 3 below.

TABLE 3

| Conductance | Total acid number (TAN) | Insulating strength [KV at 2.5 mm] |
| --- | --- | --- |
| 3.333E−04 | 0.385 | 25 |
| 3.544E−04 | 0.44 | 29 |
| 3.571E−04 | 0.519 | 32 |
| 3.544E−04 | 0.563 | 34 |
| 3.543E−04 | 0.574 | 33 |
| 4.000E−04 | 0.647 | 44 |
| 4.378E−04 | 0.659 | 44 |
| 4.368E−04 | 0.672 | 45 |
| 4.636E−04 | 0.83 | 51 |
| 5.348E−04 | 1.126 | 59 |

That is, because it is unreasonable to estimate the reduction in properties of oil by measuring only total acid number, it is preferable to make a total acid number table by additionally matching the measurement values of major physical properties, such as the viscosity of lubricating oil and the insulating strength of insulating oil, in addition to total acid number, such that the state of oil can be more precisely measured.

Figure 11:
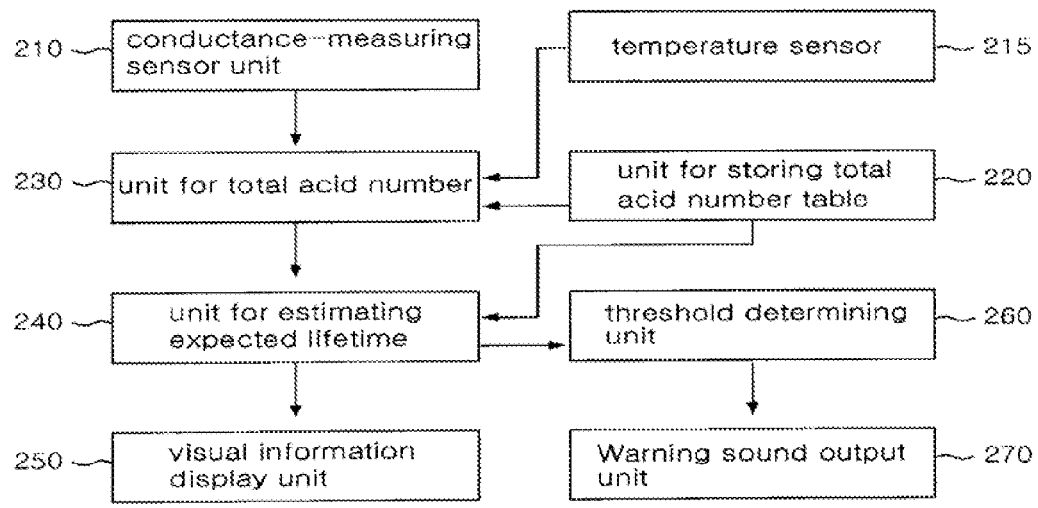
FIG. 11 is a block diagram of an apparatus for estimating the lifetime of oil through the measurement of the total acid number of oil according to another embodiment of the present invention.

FIG. 11 is a block diagram of an apparatus for estimating the lifetime of oil through the measurement of the total acid number of oil according to another embodiment of the present invention. A conductance measuring sensor unit 210 measures the conductance of oil. Herein, the conductance measuring sensor unit 210 may comprise: a substrate formed to have a given area; an electrode, patterned on the substrate and connected to a power source; and a plate-shaped conductance sensing film, which serves to measure the conductance of oil and is screen-printed continuously over the electrodes and the substrate between the electrodes and sintered. Herein, the sensing film is formed of carbon nanotubes.

The substrate may be any one selected from a glass substrate, a silicon substrate and a sintered alumina substrate, and the power source is preferably a direct current power source. The glass substrate has the advantage of low costs, but is problematic in terms of performance; the silicon substrate incurs high costs due to the need to use a cutter machine; and the sintered alumina substrate is not very expensive, and is advantageous in that it can be cut directly by a user after patterning. Thus, it is preferable to use the sintered alumina substrate.

Also, oils for use herein may include lubricant oil and insulating oil.

A temperature sensor 215 measures the temperature of oil used. Preferably, the conductance measuring sensor unit 210 can be designed such that it can operate only when the temperature measured with the temperature sensor 215 is within a specific temperature range. In the case of transformer insulating oil, the operating temperature range of the deterioration sensor is set within a range from the average temperature (more than 25° C.) to the highest coil temperature of less than 105° C. in the summer season, and is set within a range from the average temperature (more than 5° C.) to the highest coil temperature of less than 95° C. in the winter season. Values measured within this temperature range are used to examine the degree of deterioration of oil. In the case of vehicle lubricating oil, the operating temperature range of the deterioration sensor is preferably set to a range from a temperature of 40° C. after a vehicle engine warms up to the highest engine oil temperature of 120° C. Values measured in this temperature range are used to examine the degree of deterioration of oil.

A unit 220 for storing a total acid number table stores a total acid number table, in which the change in conductance and the corresponding total acid number are matched. In this case, it is preferable to store the table by additionally matching the measurement values of physical properties, in addition to the total acid number of oil. Accordingly, a unit 230 for outputting a total acid number searches the total acid number table to determine the total acid number and physical properties according to the measured conductance, and outputs the total acid number information of oil.

If the apparatus for measuring the total acid number of oil according to one embodiment of the present invention comprises the temperature sensor 215, as shown in FIG. 11, it can be constructed such that it searches the total acid number table to determine the measurement values of total acid number and physical properties according to the conductance and temperature of oil, measured in the temperature sensor 215, and outputs the information of measured total acid number and physical properties of oil. For this purpose, the total acid number table-storing unit 220 can be designed such that it stores a total acid number table, in which the change in conductance and the corresponding measurement values of total acid number and physical properties are matched according to the temperature of oil.

An expected lifetime-estimating unit 240 searches the total acid number table to determine the use period of oil, corresponding to total acid number information, and produces the estimated lifetime information of oil on the basis of the determined use period. For this purpose, the total acid number-storing unit 220 can be designed such that it classifies the measurement information about the total acid number and physical properties of oil according to the use period of oil or the running distance of vehicles injected with the oil, and stores the classified measurement information in a table. Accordingly, the expected lifetime-estimating unit 240 can estimate the use period of oil, which is used at the present, by performing a reverse-direction search in order to determine the total acid number of oil having a given use period, which corresponds to the total acid number determined in the total acid number-determining unit 230.

A visual information display unit 250 employs at least one of letters and images to visually display the estimated lifetime determined in the lifetime-estimating unit 240.

A threshold determining unit 260 produces replacement request information when the estimated lifetime information is shorter than the previously stored lifetime threshold of oil. Herein, the lifetime threshold of oil means the recommended use period of relevant oil. Thus, because the threshold can vary depending on the kind of oil that is loaded, the apparatus for estimating the oil lifetime through the measurement of total acid number of oil according to another embodiment of the present invention sets the lifetime threshold in advance depending on the kind of oil that is loaded. A warning sound output unit 270 outputs a sound message of an oil replacement warning when the replacement request information is produced.

Figure 12:
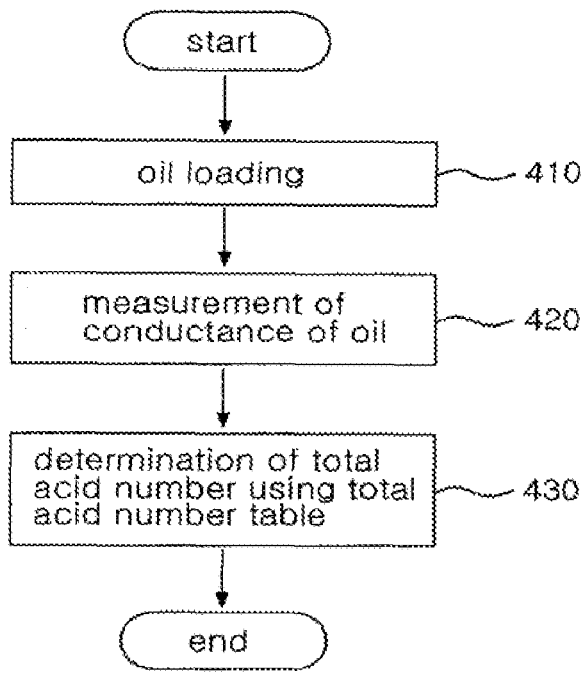
FIG. 12 is a flowchart of a method for measuring the total acid number of oil according to the present invention.

FIG. 12 is a flowchart of a method for measuring the total acid number of oil according to another embodiment of the present invention.

First, in a preparatory step for measuring total acid number, a database including a total acid number table, in which changes in oil conductance and the corresponding measurement values of total acid number and physical properties of oil are matched, is constructed. Then, oil, which is to be measured to determine the total acid number and major physical properties thereof, is loaded (step 410). When oil is injected, the injected oil comes into contact with the continuous conductance sensing film, which was screen-printed continuously on the substrate and between the electrodes and sintered. The oil injection step (step 410) is not repeated before an oil replacement time.

Then, the conductance sensing film is used to measure the conductance of oil (step 420). Finally, the total acid number, corresponding to the measured conductance, is searched for in the total acid number table, and the information about the measured total acid number and/or the physical properties of oil is outputted (step 430). In this case, when the measurement is carried out using the conductance sensing film, having a plurality of holes formed therein, the sensing density can be increased.

Figure 13:
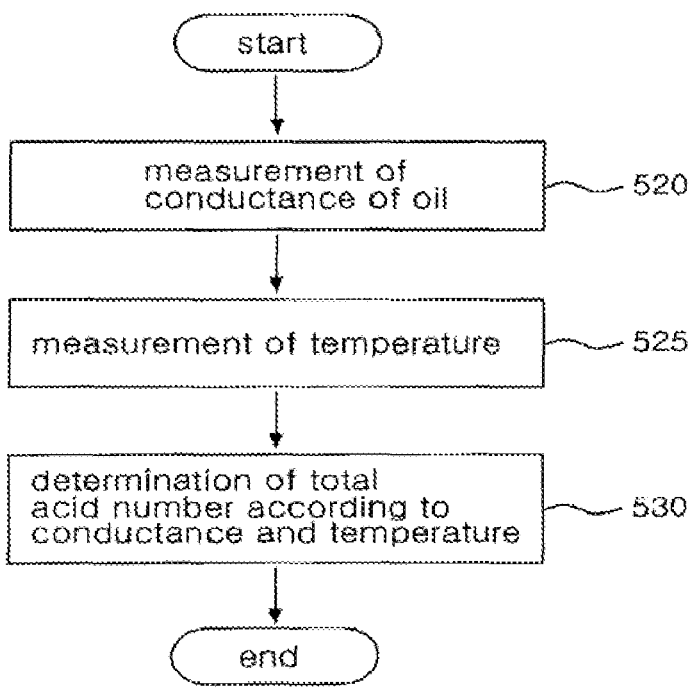
FIG. 13 is a flowchart of a method for measuring the total acid number of oil according to another embodiment of the present invention.

FIG. 13 is a flowchart of a method for measuring the total acid number of oil according to another embodiment of the present invention.

First, the conductance sensing film is used to measure the conductance of oil (step 520).

This step (step 520) may comprise a step of measuring the conductance of oil only when the temperature of oil is higher than a given temperature, for example, higher than 80° C.

Then, the current temperature of oil is measured (step 525).

Then, the information about the total acid number and physical properties, corresponding to the measured current temperature and the measured conductance of oil, is searched for in the total acid number table, and the information about the measured total acid number and the physical properties of oil is outputted (step 530). For this purpose, before the above measurement steps (steps 520-530), a step of storing a total acid number table, in which changes in conductance and corresponding measurements of total acid number and/or physical properties are matched according to the temperature of oil, is carried out.

Figure 14:
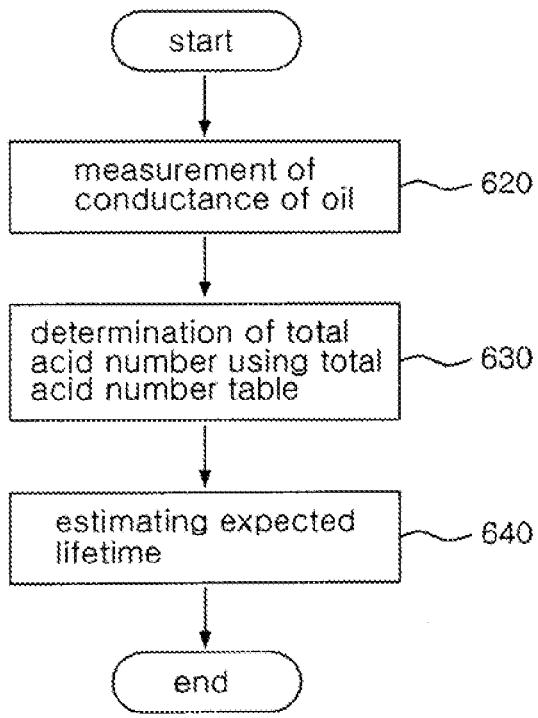
FIG. 14 is a flowchart of a method for estimating the lifetime of oil through the measurement of total acid number of oil according to another embodiment of the present invention.

FIG. 14 is a flowchart of a method for estimating the lifetime of oil through the measurement of the total acid number of oil according to another embodiment of the present invention.

First, the conductance sensing film is used to measure the conductance of oil (step 620).

This step (step 620) may comprise a step of measuring the conductance of oil only when the temperature of oil is higher than a given temperature, for example, higher than 80° C.

Then, the information about the total acid number and/or physical properties of oil according to the measured conductance is searched for in the total acid number table, and the information about the total acid number of oil is outputted (step 630).

Finally, the use period of oil, corresponding to the information about the measured total acid number and the physical properties, is searched for in the total acid number table, and the estimated lifetime information of oil is produced using the found use period (step 640). For this purpose, before the above-described steps (steps 620-640), a step of storing a total acid number table, in which changes in conductance and the use period of oil and the corresponding measurement results of total acid number and physical properties are matched is carried out.

The present invention can be conducted using software. When the invention is conducted using software, the constituent means of the present invention are code segments for practicing necessary operations. The program or code segments can be stored in program readable media or transmitted by computer data signals, coupled to carrier waves in transmission media or networks.

Recording media, which are readable by computers, include all kinds of recording units, which are readable by computer systems. Examples of recording units readable by computers include ROM, RAM, CD-ROM, DVD±ROM, DVD-RAM, magnetic tapes, floppy disks, hard disks, optical data storage units, etc. Also, recording media readable by computers can be distributed in computer systems linked by networks, so that code readable by computers can be stored in a distributed manner and executed.

Figure 15:
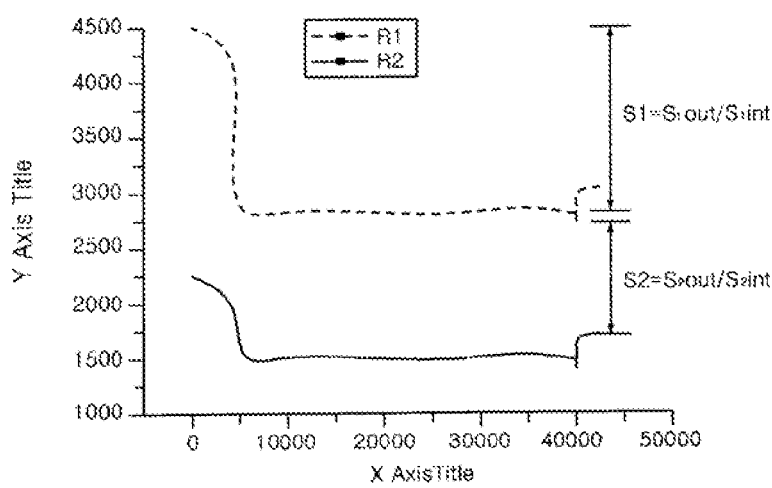
FIG. 15 is a graphic diagram showing the comparison of sensing value (Sout/Sint) in oil between inventive sensors having different initial values.

FIG. 15 is a graphic diagram showing the comparison of sensing values, obtained according to the method of making measurement using the oil sensor comprising the CNT (carbon nanotube) sensing film according to the present invention. In the prior art, there are problems in that, because the CNT sensing film is a porous material, it is difficult to reproduce the characteristics thereof upon replacement with fresh oil, and thus the characteristic patterns thereof vary depending on temperature. Herein, the oil sensor means the conductance measuring sensor unit in the construction of the present invention.

The CNT sensing film shows the change in resistance for a room-temperature state and a liquid state. Also, with respect to the initial values of the sensor, the electrical conductivity of the CNT sensing film in gases, such as air, changes by about 0.5 times $\pm\alpha$ when it is placed in liquid ($\alpha<0.1$). In the case of electrical resistance, it is changed by about 2 times ±β (β<0.2). For this reason, in order to measure the state of oil, the initial sensor value ($S_{int}$) in air is stored, a measured value ($S_{out}$) for the change in state of oil is converted to a sensing value ($S_{out}/S_{int}$), and the sensing value ($S_{out}/S_{int}$) is compared with the existing database. For comparison, before the sensing value ($S_{out}/S_{int}$) is measured, a step of constructing a database, in which the total value number is matched according to the sensing value (Sout/Sint) of the sensor, in a total acid number table, is carried out.

Herein, even when CNT sensors having different initial resistance values are used, the change in sensor value for the state of oil is similar between the CNT sensors. Thus, when the state of oil to be measured is measured as a ratio to an initial value ($S_{out}/S_{int}$), precise measurement having a relatively low error can be achieved.

Although the present invention has been described with reference to the defined embodiments and the drawings, those skilled in the art will appreciate that the present invention is not limited thereto, and that various modifications, additions and substitutions are possible, without departing from the scope and spirit of the invention as disclosed in the accompanying claims.

The invention claimed is:

1. An apparatus for measuring the total acid number of lubricant and insulating oils, the apparatus comprising:
   a unit for storing a total acid number table in which a change in conductance and the corresponding measurement values of total acid number and physical properties of oils are matched;
   a unit for measuring conductance in the oils; and
   a total acid number-determining unit for searching the total acid number table to determine the total acid number and physical properties according to the determined conductance and outputting the determined total acid number or physical properties of oils, or information about the determined total acid number or physical properties, the total acid number-determining unit communicatively coupled with the unit for storing a total acid number table and the unit for measuring conductance,
   the unit for measuring conductance including a substrate formed to have a given area, a plate-shaped conductance sensing film for measuring the conductance of oils in which the sensing film has a plurality of holes formed therein and is formed by screen-printing carbon nanotubes on the upper surface of the substrate and sintering the printed carbon nanotubes, and a vacuum deposited overlying electrode pattern extending on the upper surface of the sensing film or extending from the upper surface of the sensing film to the upper surface of the substrate connected to an external power source.

2. The apparatus of claim 1, wherein said substrate is any one selected from among a glass substrate, a silicon substrate and a sintered alumina substrate.

3. The apparatus of claim 1, wherein the external power source is a direct current power source.

4. The apparatus of claim 1, wherein the physical properties are viscosity, total base number for lubricating oil, insulating strength, water content and volume resistivity.

5. The apparatus of claim 1, wherein, when the carbon nanotubes are screen-printed, the conductance sensing film has a thickness ranging from 1 μm to 990 μm.

6. The apparatus of any one of claim 1, wherein the vacuum deposition is carried out by E-beam evaporator or sputtering.

7. An apparatus for measuring the lifetime of lubricant and insulating oils through measurement of the total acid number of the oils, the apparatus comprising:
   a unit for storing a total acid number table in which a change in conductance, the use period of oils and corresponding measurement values of total acid number and physical properties of oils are matched;
   a conductance measuring sensing unit for measuring the conductance of the oils;
   a total acid number-determining unit for searching the table to determine the total acid number and physical properties according to the measured conductance and outputting the determined total acid number or physical properties of said oils, or information about the determined total acid number or physical properties, the total acid number-determining unit communicatively coupled with the unit for storing a total acid number table and the conductance measuring sensing unit; and
   a lifetime-estimating unit for searching the total acid number table to determine the use period of oils corresponding to the total acid number information and producing estimated lifetime information about oils using the determined use period, the lifetime-estimating unit communicatively coupled with the unit for storing a total acid number table and the total acid number-determining unit,
   the unit for measuring conductance including a substrate formed to have a given area, a plate-shaped conductance sensing film for measuring the conductance of oils in which the sensing film has a plurality of holes formed therein and is formed by screen-printing carbon nanotubes on the upper surface of the substrate and sintering the printed carbon nanotubes, and a vacuum deposited overlying electrode pattern extending on the upper surface of the sensing film or extending from the upper surface of the sensing film to the upper surface of the substrate connected to an external power source.

8. The apparatus of claim 7, wherein the substrate is selected from the group consisting of a glass substrate, a silicon substrate and a sintered alumina substrate.

9. The apparatus of claim 7, wherein the external power source is a direct current power source.

10. The apparatus of claim 7, wherein the physical properties are viscosity, total base number for lubricating oil, insulating strength, water content and volume resistivity for insulating oil.

11. The apparatus of claim 7, wherein, when the carbon nanotubes are screen-printed, the conductance sensing film has a thickness ranging from 1 μm to 990 μm.

12. The apparatus of claim 7, further comprising a visual information display unit for visually displaying estimated lifetime information using at least one of letters and images.

13. The apparatus of claim 7, further comprising:
   a threshold determining unit for producing replacement request information when the estimated lifetime information is shorter than a pre-stored lifetime threshold value; and
   a warning sound output unit for outputting an oil replacement warning sound message when the replacement request information is produced.

14. The apparatus of claim 7, wherein the vacuum deposition is carried out by E-beam evaporator or sputtering.

15. A method for determining the total acid number of oils, the method comprising:
   making a unit for storing a total acid number table in which a change in conductance and the corresponding total acid number and physical properties of oils are matched;
   measuring the conductance of oils using a plate-shaped conductance sensing film having a plurality of holes formed therein and obtained by screen-printing carbon nanotubes on the upper surface of a substrate and sintering the printed carbon nanotubes, and an overlying electrode patterned using a vacuum deposition method such that it extends over the upper surface of the sensing film or extends from the upper surface of the sensing film to the upper surface of the substrate and is connected to an external power source; and searching the table to determine the total acid number or physical properties according to the measured conductance and outputting the measured total acid number or physical properties or the information of the measured total acid number or physical properties.

16. The method of claim 15, wherein the vacuum deposition method is an E-beam evaporator or a sputtering method.

17. The method of claim 15, wherein the substrate is selected from the group consisting of a glass substrate, a silicon substrate and a sintered alumina substrate.

18. The method of claim 15, wherein the external power source is a direct current power source.

19. The method of claim 15, wherein the physical properties are viscosity, total base number for lubricating oil, insulating strength, water content and volume resistivity for insulating oil.

20. The method of claim 15, wherein, when the carbon nanotubes are screen-printed, the conductance sensing film has a thickness ranging from 1 μm to 990 μm.

21. The method of claim 15, further comprising a method of making measurements using an oil sensor comprising a carbon nanotube sensing film, the method of making measurements comprising:

storing an initial sensor value Sint in air in order to measure the state of oil;

constructing, in a total acid value table, a database in which a total acid value is matched according to the sensing value Sout/Sint of the sensor;

converting a measurement value Sout for a change in the state of oil to the sensing value Sout/Sint; and comparing the sensing value Sout/Sint with information in the database.

22. An apparatus for measuring the total acid number of lubricant and insulating oils, the apparatus comprising:

a unit for storing a total acid number table in which a change in conductance and the corresponding measurement values of total acid number and physical properties of oils are matched;

a unit for measuring conductance in the oils;

a temperature sensor for measuring the temperature of said oils operating in the temperature range of 40-120 ° C; and a total acid number-determining unit for searching the total acid number table to determine the total acid number and physical properties according to the measured conductance and outputting the determined total acid number or physical properties of oils, or information about the determined total acid number or physical properties, the total acid number-determining unit communicatively coupled with the unit for storing a total acid number table and the unit for measuring conductance, the unit for measuring conductance including a substrate formed to have a given area, a plate-shaped conductance sensing film for measuring the conductance of oils in which the sensing film has a plurality of holes formed therein and is formed by screen-printing carbon nanotubes on the upper surface of the substrate and sintering the printed carbon nanotubes, and a vacuum deposited overlying electrode pattern extending on the upper surface of the sensing film or extending from the upper surface of the sensing film to the upper surface of the substrate connected to an external power source.

23. The apparatus of claim 22, wherein said glass substrate is chosen from the group consisting of a glass substrate, a silicon substrate and a sintered alumina substrate.

24. The apparatus of claim 22, wherein the external power source is a direct current power source.

25. The apparatus of claim 22, wherein the physical properties are viscosity, total base number for lubricating oil, insulating strength, water content and volume resistivity.

26. The apparatus of claim 22, wherein, when the carbon nanotubes are screen-printed, the conductance sensing film has a thickness ranging from 1 μm to 990 μm.

27. The apparatus of claim 22, wherein the vacuum deposition is carried out by E-beam evaporator or sputtering.

28. An apparatus for measuring the total acid number of lubricant and insulating oils, the apparatus comprising:

a unit for storing a total acid number table in which a change in conductance and the corresponding measurement values of total acid number and physical properties of oils are matched;

a unit for measuring conductance in the oils; and a total acid number-determining unit for searching the total acid number table to determine the total acid number and physical properties according to the measured conductance and outputting the determined total acid number or physical properties of oils, or information about the determined total acid number or physical properties, the total acid number-determining unit communicatively coupled with the unit for storing a total acid number table and the unit for measuring conductance, the unit for measuring conductance including a substrate formed to have a given area, a plate-shaped conductance sensing film for measuring the conductance of oils in which the sensing film has a plurality of holes formed therein and is formed by screen-printing carbon nanotubes on the upper surface of the substrate and sintering the printed carbon nanotubes, and a vacuum deposited overlying electrode pattern extending on the upper surface of the sensing film or extending from the upper surface of the sensing film to the upper surface of the substrate connected to an external power source.

29. The apparatus of claim 28, wherein said glass substrate is chosen from the group consisting of a glass substrate, a silicon substrate and a sintered alumina substrate.

30. The apparatus of claim 28, wherein the external power source is a direct current power source.

31. The apparatus of claim 28, wherein the physical properties are viscosity, total base number for lubricating oil, insulating strength, water content and volume resistivity.

32. The apparatus of claim 28, wherein, when the carbon nanotubes are screen-printed, the conductance sensing film has a thickness ranging from 1 μm to 990 μm.

33. The apparatus of claim 28, wherein the vacuum deposition is carried out by E-beam evaporator or sputtering.

34. An apparatus for measuring the total acid number of lubricant and insulating oils, the apparatus comprising:

a unit for storing a total acid number table in which a change in conductance and corresponding measurement values of total acid number and physical properties of oils are matched;

a unit for measuring conductance in said oils;

a temperature sensor for measuring the temperature of the oils operating in the temperature range of 40-120 ° C; and a total acid number-determining unit for searching the total acid number table to determine the total acid number and physical properties according to the measured conductance and outputting the determined total acid number or physical properties of oils, or information about the determined total acid number or physical properties, the total acid number-determining unit communicatively coupled with the unit for storing a total acid number table and the unit for measuring conductance, the unit for measuring conductance including a substrate formed to have a given area, a plate-shaped conductance sensing film for measuring the conductance of oils in which the sensing film has a plurality of holes formed therein and is formed by screen-printing carbon nanotubes on the upper surface of the substrate and sintering the printed carbon nanotubes, and has a plurality of holes formed therein, and a vacuum deposited overlying electrode pattern extending on the upper surface of the sensing film, or extending from the upper surface of the sensing film to the upper surface of the substrate and is connected to an external power source.

35. The apparatus of claim 28, wherein said glass substrate is selected from the group consisting of a glass substrate, a silicon substrate and a sintered alumina substrate.

36. The apparatus of claim 34, wherein the external power source is a direct current power source.

37. The apparatus of claim 34, wherein the physical properties are viscosity, total base number for lubricating oil, insulating strength, water content and volume resistivity.

38. The apparatus of claim 34, wherein, when the carbon nanotubes are screen-printed, the conductance sensing film has a thickness ranging from 1 μm to 990 μm.

39. The apparatus of claim 34, wherein the vacuum deposition is carried out by E-beam evaporator or sputtering.

* * * * *